United States Patent [19]

Sweeney et al.

[11] 4,060,469
[45] Nov. 29, 1977

[54] PREPARATION OF 1,1,1-TRIFLUORO-2,2-DICHLOROETHANE

[75] Inventors: Richard F. Sweeney, Elma, N.Y.; James O. Peterson, Sylvania, Ohio

[73] Assignee: Allied Chemical Corporation, N.J.

[21] Appl. No.: 753,155

[22] Filed: Dec. 21, 1976

[51] Int. Cl.² .................................................. B01J 1/10
[52] U.S. Cl. ................................ 204/163 R; 252/305
[58] Field of Search ................................ 204/163 R

[56] References Cited

U.S. PATENT DOCUMENTS 3,823,195  7/1974  Smith ................................ 204/163 R Primary Examiner—Leland A. Sebastian
Attorney, Agent, or Firm—Jay P. Friedenson

[57] ABSTRACT

1,1,1-trifluoro-2,2-dichloroethane [$CF_3CHCl_2$] is prepared by contacting 1,1,1-trifluoro-2-chloroethane [$CF_3CH_2Cl$] with a less than molar equivalent of chlorine under conditions of photochemical chlorination. The $CF_3CHCl_2$ is recovered substantially devoid of contaminating 1,1,1-trifluoro-2,2,2-trichloroethane [$CF_3CCl_3$] by-product.

14 Claims, No Drawings

PREPARATION OF 1,1,1-TRIFLUORO-2,2-DICHLOROETHANE

BACKGROUND OF THE INVENTION

1. Field of the Invention:

The present invention relates to a process for the preparation of 1,1,1-trifluoro-2,2-dichloroethane, namely, $CF_3CHCl_2$, and, more especially, relates to the preparation of 1,1,1-trifluoro-2,2-dichloroethane by the photochemical chlorination of 1,1,1-trifluoro-2-chloroethane [$CF_3CH_2Cl$] under certain critically defined reaction parameters.

2. Description of the Prior Art:

1,1,1-trifluoro-2,2-dichloroethane, is a known compound. This chlorofluorocarbon is of value as an aerosol propellant, particularly as a stratospherically safe aerosol propellant. And the thermal chlorination of 1,1,1-trifluoro-2-chloroethane too has been described in the prior art. Compare E. T. McBee et al, Ind. & Engineering Chem., 39, 409 (1947), wherein the thermal chlorination of 1,1,1-trifluoroethane [$CF_3CH_3$] has been shown to proceed in the following stepwise manner:

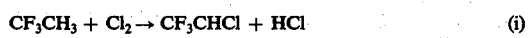

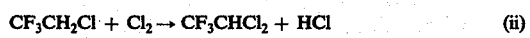

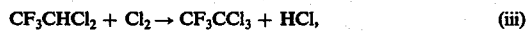

and wherein the reaction sequence [ii] can be said to represent the chlorination of interest.

However, McBee et at report that the molar ratio of chlorine to 1,1,1-trifluoroethane was approximately 1:1, and that the molar ratio of 1,1,1-trifluoro-2,2,2-trichloroethane [$CF_3CCl_3$] to the subject 1,1,1-trifluoro-2,2-dichloroethane in their recovered product ranged from 1.1 to 1.4. This of course, reflects that the rate of chlorination of 1,1,1-trifluoro-2,2-dichloroethane to yield 1,1,1-trifluoro-2,2,2-trichloroethane is considerably faster than the rate of chlorination of 1,1,1-trifluoro-2-chloroethane to yield the desired 1,1,1-trifluoro-2,2-dichloroethane. Accordingly, there exists a need in the art to provide a facile process for the preparation of the valuable chlorofluorocarbon, 1,1,1-trifluoro-2,2-dichloroethane, with only minimal production of the more highly chlorinated by-product 1,1,1-trifluoro-2,2,2-trichloroethane.

SUMMARY OF THE INVENTION

It is, therefore, a primary object of the invention to provide a process for the preparation of 1,1,1-trifluoro-2,2-dichloroethane which avoids the difficulties and shortcomings of the prior art processes.

Another object of the invention is to provide a process for the preparation of 1,1,1-trifluoro-2,2-dichloroethane by the photochemical chlorination of 1,1,1-trifluoro-2-chloroethane under certain critically defined reaction conditions.

Yet another object of the invention is to provide for the photochemical chlorination of 1,1,1-trifluoro-2-chloroethane under such critically defined reaction conditions as to provide high yields of 1,1,1-trifluoro-2,2-dichloroethane with concomitant minimal [less than about 1%] by-production of the perhalogenated compound, 1,1,1-trifluoro-2,2,2-trichloroethane.

DETAILED DESCRIPTION OF THE INVENTION

It has now been determined according to the invention that the photochemical chlorination of 1,1,1-trifluoro-2-chloroethane can unexpectedly be conducted such as to provide high yields of 1,1,1-trifluoro-2,2-dichloroethane, with only minimal amounts [less than about 1 mole percent] of by-product 1,1,1-trifluoro-2,2,2-trichloroethane, by contacting a less than molar equivalent of chlorine with 1,1,1-trifluoro-2-chloroethane vapor in a suitable reaction zone. The gas stream exiting the reaction zone is condensed in a low temperature condenser and fed to a reboiler or to an intermediate point in a fractionating column. The reboiler contents essentially consist of the 1,1,1-trifluoro-2,2-dichloroethane (b.p. 27° C.) and the 1,1,1-trifluoro-2-chloroethane (b.p. 6° C.), and same are next refluxed through a multiplate fractionating column at such a rate as desirably to maintain the overhead mix at a minimum of 99% of 1,1,1-trifluoro-2-chloroethane. The 99% concentration of the $CF_3CH_2Cl$ in the overhead mix is not essential; however, the higher its concentration and the lower the concentration of $CF_3CHCl_2$ in such mix, the already minimal by-production of the undesired $CF_3CCl_3$ is even more dramatically reduced. The preferred ratio of $CF_3CH_2Cl$ to $CF_3CHCl_2$ in the mix is greater than 90:1. The vapor exiting the fractionating column is mixed with incoming feed 1,1,1-trifluoro-2-chloroethane and chlorine, and passed through the reaction zone.

The reaction zone advantageously consists of a water-cooled condenser, maintained at a temperature sufficient to condense the 1,1,1-trifluoro-2,2-dichloroethane. A well within this condenser jacket contains a white light source of a type which will photolyze chlorine. Desirably the reaction zone is maintained at a temperature between about 5° and 175° C., and preferably is maintained between about 25° and 90° C., with room temperature [25° C.] being the most preferred. Thus, the reaction zone consists of that volume in which a gaseous mixture containing $CF_3CH_2Cl$ and chlorine are irradiated by light. The function of the water-cooled condenser is to condense $CF_3CHCl_2$ product and prevent it from entering the reaction zone, but to allow the lower boiling starting material ($CF_3CH_2Cl$) to pass into the reaction zone.

As heretofore mentioned, there are several critical parameters in the process of the invention which determine the ultimate ratio of the 1,1,1-trifluoro-2,2-dichloroethane to the by-product 1,1,1-trifluoro-2,2,2-trichloroethane:

First, the flow rate of the reactant chlorine gas must be carefully regulated and controlled so that the molar ratio of chlorine to 1,1,1-trifluoro-2-chloroethane in the reaction zone does not exceed about 0.75, and which is preferably maintained in the range of between about 0.25 and 0.50.

Second, it is virtually necessary that the feed rate of fresh 1,1,1-trifluoro-2-chloroethane entering the reactor and the boil-up rate of same in the reboiler be adjusted to provide a residence time in the reaction zone of between about 0.1 and 60 seconds, preferably between about 1 and 5 seconds. Too short a residence time can lead to unreacted chlorine being entrained, condensed in the low temperature condenser, and carried into the reboiler. The optimum residence time is in part dependent on the intensity of the light source. The light source preferably has a radiation maximum between about 2700° and 5000 A, more preferably between about 3000 A and 4000 A, most preferably between about 3000 A and 3300 A, and desirably is filtered to minimize any radiation below 3000 A, which latter radiation is degradative and gives rise to the formation of the objectionable by-product. No advantage accrues from using radiation with wavelengths above 5000 A. In general, any white light source filtered by Pyrex glass would be satisfactory; thus, the specific light source used in the photochlorination reaction is not critical. The photochlorination reaction will take place while the reaction mixture is exposed to any source of actinic radiation. Actinic radiation may be defined as the action of any light which effects chemical change. Hence, any form of light which effects chemical reaction may be employed, such as ordinary sunlight, ultraviolet light, commercial incandescent light and fluorescent light.

In order to further illustrate the present invention and the advantages thereof, the following specific example is given, it being understood that same is intended only as illustrative and in nowise limitative.

EXAMPLE

Utilizing the foregoing described equipment, 1,1,1-trifluoro-2-chloroethane at 1.36 moles/hr. and chlorine at 0.68 moles/hr. are fed to the reaction zone and there photolyzed by means of filtered white light. Unreacted 1,1,1-trifluoro-2-chloroethane passing through the reaction zone is condensed in the low temperature (−76° C.) condenser and returned to the reboiler, or to an intermediate point in the fractionating column. 1,1,1-trifluoro-2,2-dichloroethane formed by the photochlorination is condensed in the water-cooled condenser (+15° C.) and flowed back down into the jacketed fractionating column. After the first three hours of operation, a quantity of 1,1,1-trifluoro-2,2-dichloroethane has accumulated in the reboiler. The boil-up rate is adjusted to give a molar ratio of 1,1,1-trifluoro-2-chloroethane to chlorine in the reaction zone of 3:1. At the end of eight hours the reaction is terminated. Gas chromatographic analyses of the reboiler contents reveals the reaction product to consist of 1,1,1-trifluoro-2,2-dichloroethane, with less than about 1% 1,1,1-trifluoro-2,2,2-trichloroethane and 1,1,1-trifluoro-2-chloroethane starting material.

Thus, it will be appreciated that the process of this invention unexpectedly provides surprisingly high yields of the desired 1,1,1-trifluoro-2,2-dichloroethane propellant, with only minimal formation of the more highly chlorinated 1,1,1-trifluoro-2,2,2-trichloroethane by-product.

While there have been shown and described and pointed out the fundamental novel features of the invention as applied to the preferred embodiment, those skilled in the art will appreciate that various modifications, changes and omissions in the preparation of 1,1,1-trifluoro-2,2-dichloroethane illustrated and described can be made without departing from the spirit of the invention. It is the intention, therefore, to be limited only by the scope of the following claims.

What is claimed is:

1. A process for the preparation of 1,1,1-trifluoro-2,2-dichloroethane, comprising photochlorinating 1,1,1-trifluoro-2-chloroethane in a reaction zone with a less than molar equivalent of chlorine in the presence of actinic radiation, and with a residence time in the chlorine/1,1,1-trifluoro-2-chloroethane reaction zone of such duration that essentially no unreacted chlorine is entrained in the reaction effluent, but of insufficient duration as to effect other than minimal by-production of perhalogenated contaminant.

2. The process as defined by claim 1, wherein the less than molar equivalent of chlorine does not exceed about 0.75.

3. The process as defined by claim 2, wherein the less than molar equivalent of chlorine is in the range of between about 0.25 and 0.50.

4. The process as defined by claim 2, wherein the residence time in the reaction zone ranges from between about 0.1 and 60 seconds.

5. The process as defined by claim 4, wherein the residence time in the reaction zone ranges from between about 1 and 5 seconds.

6. The process as defined by claim 4, wherein the chlorine is white light photolyzed.

7. The process as defined by claim 6, wherein the white light has a radiation maximum of about 5000 A and is filtered to minimize radiation below about 3000 A.

8. The process as defined by claim 1, wherein the actinic radiation has a radiation maximum between about 2700 A and 5000 A.

9. The process as defined by claim 8, wherein the actinic radiation has a radiation maximum between about 3000 A and 4000 A.

10. The process as defined by claim 9, wherein the actinic radiation has a radiation maximum between about 3000 A and 3300 A.

11. The process as defined by claim 1 conducted at a temperature between 5 and 175° C.

12. The process as defined by claim 11 conducted at a temperature between 25° and 90° C.

13. The process as defined by claim 11 conducted at about room temperature.

14. The process as defined by claim 4, further including recycling a portion of the reaction zone effluent to the feed 1,1,1-trifluoro-2-chloroethane and chlorine.

* * * * *